United States Patent [19]
Scoville, Jr. et al.

[11] Patent Number: 5,900,256
[45] Date of Patent: May 4, 1999

[54] HYDROGEN PEROXIDE DISINFECTING AND STERILIZING COMPOSITIONS

[75] Inventors: John R. Scoville, Jr., Parker; Inna A. Novicova, Aurora, both of Colo.

[73] Assignee: Cottrell, Ltd., Englewood, Colo.

[21] Appl. No.: 09/024,881

[22] Filed: Feb. 17, 1998

Related U.S. Application Data

[63] Continuation of application No. 08/715,337, Sep. 18, 1996, abandoned.

[51] Int. Cl.$^6$ .......................... A01N 59/00; A01N 37/02; A01N 25/22
[52] U.S. Cl. .......................... 424/616; 424/126; 514/557; 514/970; 514/973; 422/28; 422/29; 252/186.29; 252/394
[58] Field of Search .................................... 424/616, 126; 514/557, 970, 973; 422/28, 29; 252/186.29, 186.38, 186.43, 387, 394

[56] References Cited

U.S. PATENT DOCUMENTS

| | | | |
|---|---|---|---|
| 3,425,954 | 2/1969 | Ruzevick et al. | |
| 3,535,240 | 10/1970 | Lyness | 252/8.55 |
| 4,557,898 | 12/1985 | Greene et al. | 422/28 |
| 5,077,008 | 12/1991 | Kralovic et al. | |
| 5,139,788 | 8/1992 | Schmidt | 424/616 |
| 5,538,152 | 7/1996 | Fontana | 216/108 |
| 5,578,134 | 11/1996 | Lentsch et al. | |
| 5,800,732 | 9/1998 | Coughlin et al. | 252/180 |

OTHER PUBLICATIONS

Alasri, A. et al., "Sporocidal properties of peracetic acid and hydrogen peroxide, alone and in combination, in comparison with chlorine and formaldehyde for ultrafiltration membrane disinfection," *Can. J. Microbiol.* 39:52–60 (1993).

Flemming, H–C., "Peracetic Acid as a Disinfectant—A Review," *Zbl. Bakt. Hyg.*, Section I, Orig. B 179:97–111 (1984).

Schön, K. et al., "Fully Automatic Cleaning and Disinfectin of Flexible Endoscopes," *Hyg. + Med.* 13:309–312 (1988).

Zhang, C. et al., "Research on the Stabilizing Action of Three Common Peracetic Acid Stabilizers," *J. West China Univ. Med. Sci.* 22(2):219–222 (1991) (Abstract only).

FMC Brochure, "FMC's Peracetic Acid Sanitizer—VigorOx™" (1993).

Johnson & Johnson Brochure, "Nu–Cidex" (1994).

*Primary Examiner*—John Pak
*Attorney, Agent, or Firm*—Townsend and Townsend and Crew LLP

[57] ABSTRACT

An aqueous acidic disinfecting and sterilizing composition for medical instruments, which may include brass, copper, aluminum, stainless steel, plastic and ceramic components. The composition contains hydrogen peroxide, peracetic acid, a corrosion inhibitor system, a surfactant and a stabilizer. These compositions have in use stability and are effective as a disinfectant and/or sterilant either at room or when heated. For other applications, surfactants, sequestering agents and stabilizers may be optional.

8 Claims, No Drawings

HYDROGEN PEROXIDE DISINFECTING AND STERILIZING COMPOSITIONS

This application is a continuation of Ser. 08/715,337, filed Sep. 18, 1996, now abandoned.

FIELD OF THE INVENTION

This invention relates to hydrogen peroxide compositions which are useful for disinfection and sterilization of metal, ceramic, polymeric and elastomeric surfaces, especially medical and dental equipment. These compositions are particularly useful for sterilization of flexible lensed endoscopy instruments, inhalation therapy equipment, and instruments and materials that can not be heat sterilized.

BACKGROUND OF THE INVENTION

A number of chemical disinfectants and sterilants are in use in healthcare institutions, including ethylene oxide, compositions of aldehydes, especially, formaldehyde, and dialdehyde (e.g., glutaraldehyde). More recently, hydrogen peroxide solutions have found a limited use for disinfection. Disinfection, as used herein, refers to the destruction of vegetative microorganisms and viruses and typically some spores; sterilization refers to the total destruction of all life forms, specifically, including spores.

Hydrogen peroxide ($H_2O_2$) is known as a potent non-irritating germicide that has been used as a topical antiseptic, especially in a 3% aqueous solution. However, hydrogen peroxide solutions are known to be corrosive to metal and inherently unstable. Practitioners in the art have sought to utilize higher concentrations of hydrogen peroxides for disinfection and sterilization of medical instruments while attempting to control its corrosiveness to metals and improve stability. Hydrogen peroxide decomposes to water and oxygen. This process is catalyzed by the enzyme catalase, which is present in organic matter such as that which is typically found on instruments after medical or dental procedures. This organic matter if not removed during routine instrument cleaning will accelerate the decomposition process and ultimately shorten the useful life of the germicide solution.

The stability of hydrogen peroxide is known to be enhanced by the presence of acids which are believed to denature and therefore prevent the catalytic effect of the catalase. U.S. Pat. No. 4,051,059, incorporated herein by reference, describes a peroxyacid antimicrobial composition of hydrogen peroxide, peracetic acid, acetic acid and a surfactant such as sulfonates or sulfates. Similarly, U.S. Pat. No. 5,200,189, the disclosure of which is incorporated herein by reference, describes a peroxyacid antimicrobial composition comprised of a C1–C4 peroxycarboxylic acid, hydrotrope coupling agent, and hydrogen peroxide. Such solutions, however, are too corrosive to be useful in a number of environments.

Still other compositions have been described which include hydrogen peroxide in conjunction with a substituted aminobenzaldehyde as an organic stabilizer and mineral acid, as an etching agent. See, U.S. Pat. No. 4,875,973, incorporated herein by reference. Alternatively, antimicrobial compositions are provided in U.S. Pat. No. 5,077,008, incorporated herein by reference, in which a strong oxidizing agent is combined with peracetic acid; chlorine releasing compounds; a copper and brass corrosion inhibitor in the form of triazoles, azoles, and benzoates; a buffering agent; a carbon steel and aluminum corrosion inhibitor in the form of chromates, borates, dichromates, molybdates, vanadates, phosphates, and tungstates; a wetting agent; and a sequestering agent. This composition is designed to be dissolved in water and utilized with a sterilizer device to control process temperature, fluid pressure, contact time, and water purity.

Other peroxides have also been described for use as preservatives, sterilants or disinfectants. U.S. Pat. No. 5,147,884, incorporated herein by reference, describes a preservative for aqueous products and systems comprising tert-butyl hydroperoxide, a monophenyl glycol ether, an organic solvent or mixture of water and organic solvent, a biocide in the form of non-halogenated phenol, a urea derivative and a surface active agent.

Compositions which have addressed both the stability and corrosiveness of the hydrogen peroxide/organic peracids have also been described. In particular, U.S. Pat. No. 4,518,585 provides hydrogen peroxide compositions (ENDO-SPOR®) which are noted to be stable with reuse over an extended period of time. The disinfectant and sterilizing solution described comprises hydrogen peroxide, a surfactant compatible with hydrogen peroxide, an aqueous-alcoholic mixture of a tertiary amine and a fatty acid alkanolamide, and an organic triazole corrosion inhibitor which is non-irritating with in-use stability.

A number of corrosion inhibitors are known to be only slightly soluble in aqueous solutions and the effectiveness of the overall composition is therefore limited.

What is needed in the art are new compositions which are useful for disinfecting and sterilizing metal, ceramic, polymeric and elastomeric surfaces, especially medical and dental equipment, but which are stable for longer shelf-life and under heavy organic loading and which provide increased anti-corrosive properties. Surprisingly, the present invention provides such compositions.

SUMMARY OF THE INVENTION

In one aspect, the present invention provides an aqueous disinfecting composition comprising of by weight an admixture of:

(a) from about 0.5 to about 50 percent of hydrogen peroxide;

(b) from about 0.001 to about 10 percent of an acid system comprising at least one organic or inorganic acid;

(c) a corrosion inhibitor system comprising from about 0.1 to about 30 percent of 1,2,3-benzotriazole and an alkylene glycol which is present in an amount of from about one to about ten times the amount of the 1,2,3-benzotriazole; and (d) the balance a diluent.

In other aspects, the present invention provides methods for the preparation of the above compositions as well as methods for using the above compositions.

DETAILED DESCRIPTION OF THE INVENTION

The present invention provides non-irritating and non-corrosive hydrogen peroxide disinfecting and sterilizing compositions. These compositions are stable in the presence of organic matter and maintain full antimicrobial effectiveness on repeated use at ambient and elevated temperatures over an extended period of time. Additionally, the compositions are non-corrosive to most metals (i.e., copper, brass, bronze, aluminum, carbon steel, stainless steel) without the need for alcohol in the compositions of the present invention which unexpectedly and advantageously utilize an alkylene glycol to solubilize the 1,2,3-benzotriazole, are thus capable of high corrosion inhibition because of the ability to use any amount of 1,2,3-benzotriazole without the deleterious effects due to its insolubility in water. The present compositions are capable of rapid disinfection and sterilization and provide improved performance over other hydrogen peroxide compositions. Yet another benefit for the present compositions is their stability during storage for periods of time up to two years and more while maintaining concentrations of hydrogen peroxide/organic acid which are sufficient to maintain disinfectant and sterilization properties, even under conditions involving high temperature and/or high loads of organic matter. Still further, the present disinfecting and sterilizing compositions are reusable under heavy organic load (minimum 5%) for periods of time in excess of 6 weeks.

Hydrogen Peroxide Compositions

The compositions of the present invention comprise by weight an admixture of:

(a) from about 0.5 to about 50 percent of hydrogen peroxide;

(b) from about 0.001 to about 10 percent of an acid system comprising at least one organic or inorganic acid;

(c) a corrosion inhibitor system comprising 1,2,3-benzotriazole in an amount of from about 0.1 to about 30 percent and an alkylene glycol which is present in an amount of from about one to about ten times the amount of the 1,2,3-benzotriazole; and (d) the balance a diluent.

The hydrogen peroxide used in the present compositions is typically a commercially available solution (having from 10–50 weight % in water). Preferably, the concentration of hydrogen peroxide in the present mixtures is from 3 to about 9% by weight of the composition, and more preferably 6–8%. While mixtures with concentrations of hydrogen peroxide above 8% by weight are advantageously used, they typically result in more difficulty in shipping under normal regulations, e.g. classified as "hazardous". A particularly preferred range of concentration of hydrogen peroxide noted above can be achieved by dilution of more concentrated commercially available forms, for example 35% and 50% hydrogen peroxide. Inorganic additives which are used as stabilizers in commercial hydrogen peroxide solutions do not adversely affect the present compositions.

A second component of the present compositions is an acid system comprising one or more organic and/or inorganic acids. The acid is present in an amount of from 0.001 to about 10% by weight. Preferably, the acid is an organic acid, more preferably a carboxylic acid or carboxylic peracid. A number of carboxylic acids and carboxylic peracids can be used, including for example, C1–C4 carboxylic acids and C1–C4 carboxylic peracids. Examples of suitable C1–C4 carboxylic acids include formic acid, acetic acid, propionic acid, glycolic acid, and succinic acid. Examples of suitable C1–C4 carboxylic peracids are those which are derived from a C1–C4 carboxylic acid or dicarboxylic acid by reacting the acid with hydrogen peroxide. Preferable C1–C4 carboxylic peracids for use in the composition of the invention include performic, peroxyacetic acid, peroxypropionic acid, peroxyglycolic acid, peroxysuccinic acid, or mixtures thereof. The carboxylic acid and peracid components are commercially available, or in the case of the peracids, can be prepared by oxidation of the carboxylic acids.

A preferred concentration range of an acid or peracid is from about 0.05% to about 10% by weight of the composition. A particularly preferred range of concentration of, for example, peracetic acid is from 0.1% to about 0.3% which is achieved by dilution of more concentrated commercially available forms, for example, 35% peracetic acid. In the present compositions peracetic acid serves as a generator of hydrogen peroxide through reversible chemical reactions, and also acts as an active ingredient and as an acidifier.

A corrosion inhibitor system is another component of the present compositions. Suitable corrosion inhibitor systems include 1,2,3-benzotriazole, and optionally one or more of the following: lower alkyl benzotriazole, hydroxybenzotriazole, lower alkyl hydroxybenzotriazole, carboxybenzotriazole, lower alkyl carboxybenzotriazole, benzimidazole, lower alkyl benzimidazole, hydroxybenzimidazole, lower alkyl hydroxybenzimidazole, carboxybenzimidazole, lower alkyl carboxybenzimidazole, mercaptobenzothiazole, lower alkyl mercaptobenzothiazole, hydroxymercaptobenzothiazole, lower alkyl hydroxymercaptobenzothiazole, carboxymercaptobenzothiazole, lower alkyl carboxymercaptobenzothiazole, sodium gluconate, sodium benzoate, butyl benzoate, monoethanolamine, triethanolamine, morpholine, sorbitol, erythritol, sodium phosphate, sodium tripolyphosphate, tetrasodium pyrophosphate, sodium molybdate, sodium nitrite, sodium bisufite, sodium metabisulfite, chromates, borates, and combinations thereof. As used herein, the term "lower alkyl" refers to a hydrocarbon group having from one to six carbon atoms, in a linear or branched chain, saturated or unsaturated.

Those compositions which are to be used for treating instruments containing copper, brass, bronze or multiple metal systems will preferably contain a corrosion inhibitor which is 1,2,3-benzotriazole on one or more of lower alkyl benzotriazole, hydroxybenzotriazole, lower alkyl hydroxybenzotriazole, sodium molybdate, sodium nitrite, sodium bisufite, sodium metabisulfite, chromates, borates, and combinations thereof. In particularly preferred embodiments, the corrosion inhibitor system is a combination of 1,2,3-benzotriazole, sodium molybdate and sodium nitrite.

For compositions intended to be used for treating devices containing carbon steel and stainless steel, several corrosion inhibitors may be suitable. Those inhibitors which have been tested and found to be effective are, e.g., sodium benzoate, sodium nitrite and sodium molybdate. Effective corrosion inhibitors should not be limited to those discussed. An effective corrosion inhibiting system will incorporate one or more inhibitors. A preferred corrosion inhibiting system for compositions intended for treatment of medical and/or dental instruments containing carbon steel and/or stainless steel will comprise sodium nitrite and sodium molybdate.

The total amount of corrosion inhibitor present in the above compositions will typically be 0.1 to about 30% by weight. Preferably the amount of 1,2,3-benzotriazole will be of from 0.1 to about 3.0%, and more preferably from 0.5 to about 2.0%.

The presence of corrosion inhibitors in amounts of from about 1.0 to about 3.0% often results in difficulties due to insolubility of the corrosion inhibitor in especially strong acid aqueous solutions. Thus, the present invention further comprise solubilizing agents in the form of alkylene glycols. As used herein, the term "alkylene glycols" refers to glycols such as, for example, ethylene glycol, propylene glycol, dialkylene glycols (e.g., diethylene glycol), trialkylene glycols (e.g., triethylene glycol), as well as the corresponding mono- and dialkyl ethers thereof, in which the alkyl ethers are lower alkyl ethers having of from one to six carbon atoms (e.g., methyl, ethyl or propyl ethers). In particularly preferred embodiments, the present invention contains propylene glycol as a solubilizing agent which is present in an amount of from about 3 to about 10 times the amount of the corrosion inhibitor. Most preferably, the corrosion inhibitor system comprises 1,2,3-benzotriazole which is present in about 1% by weight and propylene glycol which is present in about 3.5 to 6.5% by weight.

The balance of the composition, to make up 100%, includes any optional components and a diluent such as water. Preferably, the composition will have a pH of below about 5, more preferably below about 3. Typically, this pH range is achieved upon mixing the above components in the indicated amounts. When necessary, additional amounts of acid can be added to achieve the desired pH.

Other components which are optionally present in the compositions will include other stabilizers, surfactants and chelating agents.

Stabilizing agents, or stabilizers, for hydrogen peroxide mixtures are known, and include, 8-hydroxyquinoline, sodium pyrophosphate, stannic acid, sulfolene, sulfolane, sulfoxides, sulfones, sulfonic acids and others. In the present compositions, 8-hydroxyquinoline is a preferred stabilizing agent. Preferably, the compositions of the invention contain from about 0.001 to about 0.5 weight-percent of 8-hydroxyquinoline which also has some biocidal ability and may further enhance the antimicrobial activity of the composition. A sufficient amount of stabilizer should be used in order to maintain the proper amount of hydrogen peroxide during storage and reusable periods and to prevent any depression in the biocidal activity of hydrogen peroxide.

The present compositions will optionally contain up to about 30 weight-percent of a surfactant. Any surfactant which is compatible with hydrogen peroxide in acidic aqueous media, that is, which is relatively stable against oxidation and decomposition in the presence of acidic aqueous hydrogen peroxide, can be employed. Thus, surfactants which contain moieties which are oxidizable by acidic aqueous hydrogen peroxide should be avoided. Suitable surfactants can be selected from nonionic, anionic, amphoteric or cationic classes of surfactants which are commercially available and well known in the art.

Examples of a suitable nonionic surfactant are modified oxyethylated straight chain alcohol (Plurafac FC-20; BASF Wyandote Corp.) and T-Det N 9.5 (nonylphenol phenol 9.5 mole ethylene oxide adduct; Harcross Organics, Harcross Chemicals, Inc.). A preferred nonionic surfactant is T-Det N-9.5.

Examples of suitable anionic surfactants are the alkyl sulfate salts, e.g., alkali metal alkyl sulfates, having from 8 to 18 carbon atoms such as sodium lauryl sulfate; the alkyl sulfonate salts, e.g., alkali metal alkyl sulfonates having from 8 to 22 carbon atoms such as sodium-1-decane sulfonate and sodium 2-tridecane sulfonate; and the alkylaryl sulfonate salts, e.g., alkali metal alkylaryl sulfonates such as sodium dodecylbenzenesulfonate and disodium 4-dodecylated oxydibenzenesulfonate. Other suitable anionic surfactants for use in this invention include: 1) fluorocarbon-based surfactants such as ammonium perfluoroalkyl sulfonates (Flourad FC-121; 3M Company), potassium perfluoroalkyl sulfonate (Flourad FC-95; 3M Company), and amine perfluoroalkyl sulfonate (Flourad FC-99; 3M Company); 2) linear alkyl naphthalene sulfonate (Petro BA; Bill Petrochemical Co., Inc.); 3) modified petroleum sulfonates containing auxiliary soaps (Petromixes; Witco Chemical Corp., Sonneborn Div.); 4) alkyl naphthalene sodium sulfonate (Petro P; Witco Chemical Corp.); 5) petroleum sulfonate (Petrostep, Petrostep 420, Petrostep 465; Stepan Chemical Co.); and 6) Sodium lauryl sulfate (Polystep B- 5; Stepan Chemical Co.).

A suitable amphoteric surfactant is a fluorinated alkyl amphoteric mixture sold as Fluorad FC-100 (3M Company, Minneapolis, Minn., USA).

Chelating agents can be added to the composition of the invention to enhance biological activity, cleaning performance and stability of the peroxyacids. For example, 1-hydroxyethylidene-1,1-diphosphonic acid commercially available from the Monsanto Company under the designation "DEQUEST®", EDTA (ethylenediaminetetraacetic acid), 8-hydroxyquinoline, nitrilotriacetic acid, ethyleneglycol-bis-(β-aminoethyl ether)-N,N-tetraacetic acid, copper 8-quinolinate, hexamethylenediamine tetra (methylene phosphonate) (sold as Dequest 2051, Monsanto Co., St. Louis, Mo., USA), diethylenetriamine penta (methylene phosphonic acid) (sold as Dequest 2060, Monsanto Co.), have been found suitable. Preferred chelating agents are 1-hydroxyethylidene diphosphonic acid (Dequest 2010), 8-hydroxyquinoline, and EDTA (ethylenediaminetetraacetic acid). Chelating agents can be added to the present composition to control or sequester hardness ions such as calcium and magnesium. In this manner both detergency and sanitization capability can be enhanced.

Other materials which are sufficiently stable at the low pH contemplated by the present composition may be added to the composition to impart desirable qualities depending upon the intended ultimate use. For example, phosphoric acid ($H_3PO_4$) can be added to the composition of the invention. Additional materials can be added to the composition to change its color or odor, to adjust its viscosity, to enhance its thermal (i.e., freeze-thaw) stability or to provide other qualities which tend to make it more marketable.

One of skill in the art will appreciate that for certain applications in which corrosion is not a problem, the compositions of the present invention can be prepared without a corrosion inhibitor system. For these compositions, the preferred ranges for hydrogen peroxide and an acid system are essentially as described above. Most preferably, the acid is an organic peracid, such as performic or peracetic acid. These compositions will find use, preferably in the food services industry.

Methods of Preparing Hydrogen Peroxide Compositions

The compositions of the present invention can readily be prepared by combining the individual ingredients in a desired solvent, typically water.

In a preferred embodiment, appropriate amounts of propylene glycol, 1,2,3-benzotriazole and 8-hydroxyquinoline are placed in a mixing tank/vessel and combined using smooth agitation until all components are completely dissolved. To this mixture is added about 97% of the final volume of water and mixing is continued until a homogeneous solution is obtained. An appropriate amount of peracetic acid, or other acid, is added with smooth blending, followed by slow addition of an appropriate amount of hydrogen peroxide. A suitable amount of sodium nitrite is combined with 1.25% of the water and very slowly added to the peracetic acid solution. After 0.25 to about 2.0 hr, a second solution of sodium molybdate in 1.25% of the water is added to the peracetic acid solution. Mixing is continued until a homogeneous composition is achieved.

The above methods are equally applicable to compositions prepared by substituting other components (e.g., other acids for peracetic acid, other stabilizing agents for 8-hydroxyquinoline, other chelating agents for 1-hydroxyethylidene-1,1-diphosphonic acid, etc.).

Uses for the Hydrogen Peroxide Compositions

As noted above, the present compositions are useful in the cleaning or disinfecting of equipment in the health care industries. Additionally, the compositions can be used for the sanitizing of processing facilities or equipment in the food service or food processing industries. Examples of process facilities in which the composition of the invention can be employed include a milk line dairy, a continuous brewing system, food processing lines such as pumpable food systems and beverage lines. Food service wares can also be disinfected with the composition of the invention. The composition is also useful in sanitizing or disinfecting solid surfaces such as floors, counters, furniture, medical tools and equipment found in the health care industry. Such surfaces often become contaminated with liquid body spills such as blood, other hazardous body fluids or mixtures thereof.

Generally, the actual cleaning of the in-place system or other surface (i.e., removal of unwanted organic material) is accomplished with a different material such as a formulated detergent (or this composition modified for detergent effect) which is introduced with heated water. After this cleaning step, the present compositions would be applied or introduced into the system at a suitable solution concentration in unheated, ambient temperature water. The present composition is found to remain in solution in cold (e.g., 40° F./4° C.) water and heated (e.g., 140° F./60° C.) water. Although it is not normally necessary to heat the aqueous solution of the present composition, under some circumstances heating may be desirable to further enhance its antimicrobial activity.

A method of sanitizing substantially fixed in-place process facilities comprises the following steps. The composition of the invention is introduced into the process facilities at a temperature in the range of about 4° to 60° C. After introduction of the solution, the solution is circulated throughout the system for a time sufficient to sanitize the process facilities (i.e., to kill undesirable microorganisms). After the system has been sanitized by means of the present composition, the solution is drained from the system. Upon completion of the sanitizing step, the system optionally may be rinsed with other materials such as potable water. The composition is preferably circulated through the process facilities for 10 minutes or less. Upon completion of sterilization such rinsing is usually mandatory with circulation for longer periods of time.

The composition may also be employed by dipping food processing equipment into the solution, soaking the equipment for a time sufficient to sanitize the equipment, and wiping or draining excess solution off the equipment. The composition may be further employed by spraying or wiping food processing surfaces with the solution, keeping the surfaces wet for a time sufficient to sanitize the surfaces, and removing excess solution by wiping, draining vertically, vacuuming, etc.

The composition of the invention may also be used in a method of sanitizing hard surfaces such as institutional type equipment, utensils, dishes, health care equipment or tools, and other hard surfaces. The composition may also be employed in sanitizing clothing items or fabric which have become contaminated. The composition is contacted with any of the above contaminated surfaces or items at temperatures in the range of about 4° C. to 60° C., for a period of time effective to sanitize, disinfect, or sterilize the surface or item. For example, the composition can be injected into the wash or rinse water of a laundry machine and contacted with contaminated fabric for a time sufficient to sanitize the fabric. Excess solution can then be removed by rinsing or centrifuging the fabric.

As the term "sanitizing" is used in the method of the instant invention, it means a reduction in the population numbers of undesirable microorganisms by about 5 powers of 10 or greater (i.e., at least 5 orders of magnitude) after a 30 second exposure time. The composition may also be used to achieve disinfection or sterilization (i.e., elimination of all microorganisms) by employing higher levels of peracids in the use solution. It is to be emphasized that at the lesser strengths the instant use solution provides sanitizing performance.

The following Examples are intended to illustrate the above invention and should not be construed as to narrow its scope. One skilled in the art will readily recognize that these Examples suggest many other ways in which the present invention could be practiced.

EXAMPLES

Example 1

This example illustrates the preparation of a preferred disinfectant compositions. The amounts of components are provided below.

| Ingredient | Percent by Weight |
|---|---|
| Composition I | |
| Hydrogen peroxide | 7.3 |
| Peracetic acid | 0.23 |
| 1-Hydroxyethylidene-1,1-diphosphonic acid | 0.70 |
| 8-Hydroxyquinoline | 0.0035 |
| Propylene glycol | 4.10 |
| Nonylphenol surfactant | 0.002 |
| 1,2,3-Benzotriazole | 1.00 |
| Sodium Nitrite | 0.25 |
| Sodium Molybdate | 0.25 |
| Deionized water to total 100% by weight | |
| Composition II | |
| Hydrogen peroxide | 7.0 |
| Peracetic acid | 0.35 |
| 1-Hydroxyethylidene-1,1-diphosphonic acid | 3.0 |
| Propylene glycol | 4.5 |
| 1,2,3-Benzotriazole | 1.5 |
| Sodium Nitrite | 0.25 |
| Sodium Molybdate | 0.25 |
| Deionized water to total 100% by weight | |

Each of the compositions was prepared by the general method described above.

Example 2

This example illustrates the stability and biocidal activity of Composition I of Example 1.

The composition of Example 1 was tested for biocidal activity against *Bacillus subtilis var. niger* spores and for stability of the active ingredients. Tests were conducted on the composition of this invention with and without organic load (5% calf serum) and diluted with deionized water to a ratio of 1:0.63 and 1:0.41 (see Tables 1–3). The stability of the active ingredients was conducted at room temperature and at elevated temperature (50° C.). These results are presented in Tables 4–7.

To assess the biocidal activity of the composition in Example 1, full strength and diluted compositions were exposed against *B. subtilis*, with an initial challenge level of $6.0 \times 10^7$ cfu/0.5 mL. A commercially available hydrogen peroxide disinfectant Endo-Spor®, a composition which is the subject of U.S. Pat. No. 4,518,585, (manufactured by Globe Medical, Largo, Fla., USA) was also tested for comparison purposes.

TABLE 1

| Exposure in Minutes | Colony Forming Units per mL | Exposure in Minutes | Colony Forming Units per mL |
|---|---|---|---|
| Invention Composition | | Endo-Spor ® | |
| 3.0 | 0 | 3.0 | $1.6 \times 10^6$ |
| 6.0 | 0 | 6.0 | $1.4 \times 10^6$ |
| 9.0 | 0 | 9.0 | $1.0 \times 10^6$ |
| 12.0 | 0 | 12.0 | $8.0 \times 10^5$ |
| 15.0 | 0 | 15.0 | $6.9 \times 10^5$ |

As Table 1 indicates, the present composition provides complete biocidal activity under conditions in which a commercially available preparation does not.

The data displayed in Table 2 confirms the increased effectiveness of the present invention over Endo Spor, even when diluted to less than half strength.

TABLE 2

| Exposure in Minutes | Colony Forming Units per ml | Exposure in Minutes | Colony Forming Units per ml |
|---|---|---|---|
| Composition - diluted 1:0.63 (4.5%) | | Composition - diluted 1:0.41 (3.0%) | |
| 3.0 | $5.1 \times 10^5$ | 3.0 | $9.9 \times 10^5$ |
| 6.0 | 4 | 6.0 | $2.7 \times 10^5$ |
| 9.0 | 0 | 9.0 | $5.2 \times 10^2$ |
| 12.0 | 0 | 12.0 | 0 |
| 15.0 | 0 | 15.0 | 0 |

The data displayed in Table 3 confirms the increased effectiveness of the present invention over Endo Spor, even when diluted with organic matter in the form of 5% calf serum.

TABLE 3

Compositions diluted with 5% calf serum

| Exposure in Minutes | Colony Forming Units per ml | Exposure in Minutes | Colony Forming Units per ml |
|---|---|---|---|
| Composition - diluted 1:0.63 (4.5%) | | Composition - diluted 1:0.41 (3.0%) | |
| 3.0 | $1.3 \times 10^6$ | 3.0 | $9.1 \times 10^5$ |
| 6.0 | $2.1 \times 10^5$ | 6.0 | $6.1 \times 10^5$ |
| 9.0 | $1.2 \times 10^2$ | 9.0 | $4.1 \times 10^5$ |
| 12.0 | <10 | 12.0 | $2.6 \times 10^4$ |
| 15.0 | <10 | 15.0 | $9.9 \times 10^3$ |

For stability evaluation, the compositions were undiluted, diluted with water or diluted with 5% calf serum to provide additional challenge. The compositions were held at the indicated temperatures for the noted time period and the percent hydrogen peroxide remaining was determined according to standard methods. The results are presented in Table 4 (undiluted), Tables 5 and 6 (diluted compositions) and Table 7 (serum challenged compositions).

TABLE 4

Stability of the active ingredients of Example 1 undiluted

| at 20° C.–25° C. | | at 50° C. | |
|---|---|---|---|
| Exposure by Days | Percent by weight Hydrogen Peroxide Undiluted Composition | Exposure by Days | Percent by weight Hydrogen Peroxide Undiluted Composition |
| 0 | 7.29 | 0 | 7.20 |
| 3 | 7.29 | 4 | 6.51 |
| 11 | 7.30 | 12 | 6.97 |
| 12 | 7.29 | 19 | 6.83 |
| 17 | 7.30 | | |
| 23 | 7.31 | | |
| 27 | 7.24 | | |
| 38 | 7.24 | | |
| 68 | 7.17 | | |
| 80 | 7.29 | | |
| 127 | 7.29 | | |
| 164 | 7.30 | | |
| 240 | 7.23 | | |
| 270 | 6.90 | | |

TABLE 5

Stability of active ingredients of diluted composition - Dilution: 0.6:1

| | Percent by weight active ingredients | | |
|---|---|---|---|
| Exposure by Days | Hydrogen Peroxide | Peracetic Acid | Active Oxygen |
| 0 | 4.30 | 0.017 | 2.027 |
| 45 | 4.42 | 0.136 | 2.1 |

TABLE 6

Stability of active ingredients of diluted composition - Dilution: 0.4:1

| | Percent by weight active ingredients | | |
|---|---|---|---|
| Exposure by Days | Hydrogen Peroxide | Peracetic Acid | Active Oxygen |
| 0 | 3.25 | n/a | n/a |
| 45 | 3.28 | n/a | n/a |

TABLE 7

Stability of the active ingredients of composition diluted with 5% calf serum

| at 20° C.–25° C. | | at 50° C. | |
|---|---|---|---|
| Exposure by Days | Percent by weight Hydrogen Peroxide Undiluted Composition | Exposure by Days | Percent by weight Hydrogen Peroxide Undiluted Composition |
| 1 | 6.51 | 0 | 6.51 |
| 3 | 6.81 | 3 | 6.36 |
| 4 | 6.60 | 4 | 6.51 |
| 10 | 6.42 | 10 | 6.67 |
| 24 | 6.23 | 24 | 5.72 |
| 25 | 6.54 | 25 | 6.01 |

Example 3

This example illustrates the stability of Composition II of Example 1.

The stability of the active ingredients was conducted at room temperature and at elevated temperature (60° C.).

These results are presented in Tables 8–9.

TABLE 8

Stability of Composition II at room temperature

| Exposure by hour | 0 | 24 | 96 | 144 | 720 |
|---|---|---|---|---|---|
| Concentration of $H_2O_2$ and Peracetic acid by % | 7.03 | 7.30 | 7.44 | 7.34 | 5.285 |

TABLE 9

Stability of Composition II at 60° C.

| Exposure by hour | 0 | 1 | 3 | 8 |
|---|---|---|---|---|
| Concentration of $H_2O_2$ and Peracetic acid by % | 7.03 | 7.81 | 7.13 | 3.77 |

As can be seen from the above Tables 8 and 9, compositions without stabilizers exhibited decreased amounts of hydrogen peroxide at 30 days at room temperature or at 8 hours at 60° C.

Example 4

This example illustrates the preparation of a disinfectant composition in the absence of an alkylene glycol. The amounts of components are provided below.

| Ingredient | Percent by Weight |
|---|---|
| Hydrogen peroxide | 7.5 |
| Peracetic acid | 0.25 |
| Trichloroacetic acid | 0.3 |
| 1-Hydroxyethylidene-1,1-diphosphonic acid | 3.6 |
| Glycerol | 2.0 |
| 1,2,3-Benzotriazole | 0.75 |
| Deionized water to total 100% by weight | |

While the above composition was found to be stable over a period of 30 days, the composition did not exhibit the desired anticorrosive properties. In particular, a sample of aluminum metal treated with the above composition exhibited small spots after 5 days and corrosive spots after 10 days. Similarly, stainless steel treated with the above composition exhibited dark spots after 5 days and dark corrosive spots after 10 days. This composition although stable did not produce the desired anticorrosive effect found in the preferred composition of the present invention which includes sodium molybdate and sodium nitrite.

While the invention has been described in the foregoing description, the same is to be considered as illustrative and not restrictive in character. It is to be understood that only the preferred embodiments have been described and that all changes and modifications that come within the spirit of the invention are desired to be covered.

What is claimed is:

1. An aqueous disinfecting and sterilizing anticorrosive composition comprising of by weight an admixture of:

(a) from about 6% to about 9% of hydrogen peroxide;

(b) from about 0.15% to about 0.35% of peracetic acid;

(c) from about 0.1% to about 3% of 1,2,3-benzotriazole;

(d) from about 0.05% to about 0.5% sodium nitrite;

(e) from about 0.05% to about 0.5% sodium molybdate;

(f) from about 2% to about 6% propylene glycol;

(g) from about 0.0001% to about 1.0% of a stabilizer of hydrogen peroxide;

(h) from about 0% to about 30% of a surfactant;

(i) from about 0.05% to about 10% of a chelating agent; and (j) the balance an aqueous diluent; and wherein said composition has a pH of less than about 5.

2. A composition in accordance with claim 1, wherein said surfactant is an anionic surfactant.

3. A composition in accordance with claim 2, wherein said surfactant is present in an amount sufficient to act as wetting agent.

4. A composition in accordance with claim 1, wherein said chelating agent is a phosphonate.

5. A composition in accordance with claim 4, wherein said phosphonate is 1-hydroxyethylidene-1,1-diphosphonic acid.

6. A composition in accordance with claim 1, wherein:

(a) said hydrogen peroxide stabilizer is 8-hydroxyquinoline; and (b) said chelating agent is 1-hydroxyethylidene-1,1-diphosphonic acid.

7. A composition according to claim 1, wherein said pH is less than about pH 3.

8. An aqueous anticorrosive, disinfecting and sterilizing composition comprising, by weight, about:

7.3% hydrogen peroxide;

0.23% peracetic acid;

1.00% 1,2,3-benzotriazole;

0.25% sodium nitrite;

0.25% sodium molybdate;

4.10% propylene glycol;

0.0035% 8-hydroxyquinoline; and 0.70% 1-hydroxyethylidene-1,1-diphosphonic acid, wherein said composition has a pH of less than about 5.

* * * * *